US006743022B1

(12) United States Patent
Sarel

(10) Patent No.: US 6,743,022 B1
(45) Date of Patent: Jun. 1, 2004

(54) SYSTEM AND METHOD FOR AUTOMATED SELF MEASUREMENT OF ALERTNESS EQUILIBRIUM AND COORDINATION AND FOR VENTIFICATION OF THE IDENTIFY OF THE PERSON PERFORMING TASKS

(76) Inventor: Oded Sarel, 37 Tel Zur Street, 40 500 Even Yehuda (IL)

( * ) Notice: Subject to any disclaimer, the term of this patent is extended or adjusted under 35 U.S.C. 154(b) by 0 days.

(21) Appl. No.: 09/857,377
(22) PCT Filed: Dec. 3, 1999
(86) PCT No.: PCT/IL99/00659
§ 371 (c)(1),
(2), (4) Date: Aug. 10, 2001
(87) PCT Pub. No.: WO00/33155
PCT Pub. Date: Jun. 8, 2000

Related U.S. Application Data
(60) Provisional application No. 60/110,726, filed on Dec. 3, 1998.

(51) Int. Cl.[7] .......................... G09B 19/00; G08B 29/00
(52) U.S. Cl. ...................... 434/236; 434/219; 340/5.81; 340/5.82; 340/5.83; 340/5.84; 382/115; 382/116; 382/117; 382/118
(58) Field of Search ................................ 434/236, 237, 434/238, 262, 258, 322–364, 219, 220; 382/115, 117, 116, 118; 340/5.81, 5.82, 5.84, 5.83

(56) References Cited

U.S. PATENT DOCUMENTS 3,877,466 A * 4/1975 Montor ....................... 600/545
4,196,412 A * 4/1980 Sluis et al. .................. 340/901
4,740,072 A   4/1988 Griffin et al.
5,229,764 A * 7/1993 Matchett et al. ............ 340/5.52
5,392,030 A * 2/1995 Adams ........................ 340/576
5,675,704 A * 10/1997 Juang et al. ................. 704/246
5,687,291 A   11/1997 Smyth
5,700,149 A * 12/1997 Johnson et al. ............. 434/322
5,724,987 A   3/1998 Gevins et al.
5,805,719 A * 9/1998 Pare et al. ................... 382/115
5,811,681 A   9/1998 Braun et al.
5,813,993 A * 9/1998 Kaplan et al. ............... 600/544
5,828,943 A * 10/1998 Brown ........................ 434/258
5,870,768 A * 2/1999 Hekmatpour ............. 707/501.1
5,900,827 A * 5/1999 Graham et al. ............. 340/963
5,917,415 A   6/1999 Atlas
5,940,801 A * 8/1999 Brown ........................... 705/2
5,999,909 A * 12/1999 Rakshit et al. .................. 705/2
6,014,626 A * 1/2000 Cohen ......................... 704/275
6,071,236 A * 6/2000 Iliff ............................. 600/300
6,205,233 B1 * 3/2001 Morley et al. .............. 382/103
6,229,908 B1 * 5/2001 Edmonds et al. ........... 382/124

FOREIGN PATENT DOCUMENTS

WO   WO-93/08739 A1 * 5/1993 ........... A61B/13/00

* cited by examiner

Primary Examiner—John Edmund Rovnak
(74) Attorney, Agent, or Firm—G.E. Ehrlich (1995) Ltd.

(57) ABSTRACT

A system and method for automated self measurement of alertness, equilibrium and coordination and for verification of the identity of the person being tested is provided. The system for self-tutoring and testing a person includes an identifying unit for identifying the person to be tested, at least one self-tutoring unit for instructing the person in at least one test to be performed, at least one testing unit for performing each of the at least one tests and an interpretation unit for evaluating the results of each of the at least one tests.

18 Claims, 7 Drawing Sheets

SYSTEM AND METHOD FOR AUTOMATED SELF MEASUREMENT OF ALERTNESS EQUILIBRIUM AND COORDINATION AND FOR VENTIFICATION OF THE IDENTIFY OF THE PERSON PERFORMING TASKS

This application claims the benefit of Provisional application Ser. No. 60/110,726, filed Dec. 3, 1998.

FIELD OF THE INVENTION

The present invention relates to a system and method for automated self-measurement of alertness, equilibrium and coordination.

BACKGROUND OF THE INVENTION

An individual's alertness before many operations may be critical to the efficiency and safety of the requirements. This is especially important in performing tasks, such as driving, flying an airplane, and sensitive or dangerous tasks. In addition, it is useful for employees carrying normal and relatively safe work and in other situations where an individual's alertness should be evaluated.

Employees under the influence of alcohol and drugs directly and indirectly cause damages to workplaces. In the USA it is estimated that the damages are in excess of $150 billion a year. Research has shown that when an employer carries out drugs and alcohol testing, then drug and alcohol usage is reduced to one fifth.

Currently there is a lack of automated systems that can simplify the process of detecting drugs and alcohol abuse. Furthermore, currently there is no simple way of detecting drugs and alcohol abuse without continuous and consistent testing.

Other examples where early detection is useful include prior to participating in sports, the detection of tiredness of drivers prior to long-distance journey and the detection of students whose behavior and lack of alertness indicates alcohol or drug abuse.

In many organizations, personnel are required to take tests, such as hearing and visual acuity tests, in order to meet certain regulations. In addition, these personnel are required to be tutored for safety regulations (e.g. fire regulations) or quality control regulations imposed by quality control standards, such as the ISO standard.

These assignments typically require enormous human resources in order to manage the summoning, testing, tutoring, analysis of the test results and re-summoning of the personnel in accordance with specific regulations.

One way to reduce the human resources required for these assignments is to conduct testing such that the person taking the test is self tested without additional human attendance. Such self testing systems are known in the art. For example, when performing vision tests, a testing apparatus is used which is operated by an operator who identifies the tested person, explains how to use the apparatus, administers the test, and records the test results. This procedure is time consuming, requires highly trained operators and is therefore expensive.

U.S. Pat. No. 4,740,072 to Griffin et al describes a vision testing apparatus which is operated by an operator for administering a variety of visual performance tests to a test subject. The operator of the vision testing apparatus manually operates various buttons and levers on the testing apparatus and to present a series of test slides to the test subject. The operator also has to ask the test subject various questions and to manually record the answers either on an appropriate form or alternatively initiate storage of the test results on a computer connected to the vision testing apparatus. Thus, even with computerized data storage of the test results, a qualified, trained operator must perform a substantial amount of manual operations and must verbally instruct the test subject, which is time consuming and expensive.

SUMMARY OF THE INVENTION

In a related PCT application WO98/02083 to the present inventors and incorporated herein by reference, a method and a system for automatic management of summoning, identifying, self-testing and/or self tutoring of subjects is disclosed. The method of self-tutoring can include video units, multi-media software, remote control tutoring as in telemedicine. This self-tutoring prior to self testing is applicable, for example, to visual acuity tests, intraoccular pressure visual fields, pregnancy follow-ups, spirometry, Blood pressure ECG," self-blood tests and response time. A medical condition sensing system, detailing some of the sensors, such as virtual reality glasses for visual acuity, twelve-lead ECG and spirometry are described in U.S. patent application Ser. No. 09/428,430 assigned to the present applicants, and incorporated herein by reference.

The present invention describes a system for automated self-measurement of alertness, equilibrium and coordination. The system includes an alert meter which can be used for self-tutoring and testing of various parameters, as described above.

The system using the alert meter checks individual's response speed, coordination, and the equilibrium as parameters of alertness. Alertness can be influenced by various causes: extreme tiredness, life crisis, toxic substance, alcohol, drugs (opiates) or medication. People who are not alert can fail or err in performing various tasks. The system can detect these individuals before performing the tasks and if necessary, indicate that further evaluation (i.e. alcohol levels in blood or exhale air, drug level in blood or urine) be undertaken.

The system of the present invention instructs and guides the individual, performs a series of tests, interprets the results, files and exports the results at will. The system has an option to automatically summon and/or identify the individual.

There is therefore provided, in accordance with a preferred embodiment of the present invention, a system and method for self-tutoring and testing a person. The system includes an identifying unit for identifying the person to be tested, at least one self-tutoring unit for instructing the person in at least one test to be performed, at least one testing unit for performing each of the at least one tests and an interpretation unit for evaluating the results of each of the at least one tests.

There is also provided, in accordance with a preferred embodiment of the present invention, a system and method for identifying a person being tested. The system includes an identifying unit for identifying the person to be tested, at least one testing unit for performing at least one identification test, an interpretation unit for evaluating the results of the at least one test, a storage unit for storing the results and a comparison unit for comparing the results from the interpretation unit with results previously stored in the storage unit.

In addition, there is provided, in accordance with a preferred embodiment of the present invention, a method for continuously verifying the identity of a person performing a task. The method includes the steps of:

creating and storing an initial profile of personal characteristics associated with the person, prior to performing the task;

continuously performing at least one identification test at random intervals while the person performs the task;

storing the results of each of the randomly performed at least one identification test; and comparing the results of each of the randomly performed at least one identification test with the initial profile and with the previous randomly performed tests after each randomly performed at least one identification test.

Furthermore, in accordance with a preferred embodiment of the present invention, the test comprises one of a group of tests including a person's alertness, steadiness, co-ordination and response time.

Furthermore, in accordance with a preferred embodiment of the present invention, if the results of the automatic comparison match the identification test with the initial profile, the method further includes the step of allowing the person to perform the task.

Furthermore, in accordance with a preferred embodiment of the present invention, the method further includes the step of comparing the initial profile of personal characteristics with a database of personal characteristics of a group of persons to ascertain the identity of the person. The profile includes at least one of a set of parameters including voice recognition patterns, iris patterns and photographic images.

Furthermore, in accordance with a preferred embodiment of the present invention, the method further includes the step of storing the results.

Furthermore, in accordance with a preferred embodiment of the present invention, the method further includes the step of evaluating the tests in relation to the stored results. The step of evaluating is operable in real time or off-line.

Furthermore, in accordance with a preferred embodiment of the present invention, the step of evaluating includes the step of determining whether a person is under the influence of external substances or stimulants.

Additionally, in accordance with a preferred embodiment of the present invention, the step of evaluating includes evaluating the results of the tests individually and/or in any combination of tests.

In addition, there is provided, in accordance with a preferred embodiment of the present invention, a method for automatically summoning and automatically verifying the identity of the person being summoned. The method includes the steps of:

constructing a profile database of parameters associated with a group of persons;

preparing a schedule for summoning at least one person from the group;

at the scheduled time, automatically performing at least one identification test;

verifying the results of the at least one identification test to determine the identity of the person attending at the scheduled time.

If the identification profile details of the person attending match the identification profile details of the person for the scheduled time, the operations scheduled for the person being summoned can be performed.

Furthermore, in accordance with a preferred embodiment of the present invention, the method further includes the step of evaluating the results of the performing the operations.

Furthermore, in accordance with a preferred embodiment of the present invention, wherein if the identification details of the person attending do not match the identification details of the person for the scheduled time but match the identification details of another one of the group of persons, the operations scheduled for the person being summoned can be performed; or a further appointment for the identified person can be scheduled.

In addition, there is provided, in accordance with a preferred embodiment of the present invention, a method for continuously verifying the identity of a person performing a task. The method includes the steps of:

creating and storing an initial profile of personal characteristics associated with the person prior to performing the task;

performing at least one identification test at random intervals while the person performs the task;

storing the results of each of the randomly performed at least one identification test; and comparing the results of each of the randomly performed at least one identification test with the initial profile at the completion of the task.

The profile includes at least one of a set of parameters including voice recognition patterns, iris patterns and photographic images.

Finally, there is provided, in accordance with a preferred embodiment of the present invention, a method for validating a person's comprehension of a document, the method comprising the steps of:

requesting the person to read the document;

randomly asking at least one question, from a group of questions, related to the document; and analyzing the answer to the at least one question.

The method may further include the steps of:

requesting the person to re-read the document; and repeating the steps of randomly asking at least one question and analyzing the answer to the question until the person's response indicates comprehension of the document.

BRIEF DESCRIPTION OF THE DRAWINGS

The present invention will be understood and appreciated more fully from the following detailed description taken in conjunction with the appended drawings in which.

DESCRIPTION OF THE PRESENT INVENTION

Figure 1:
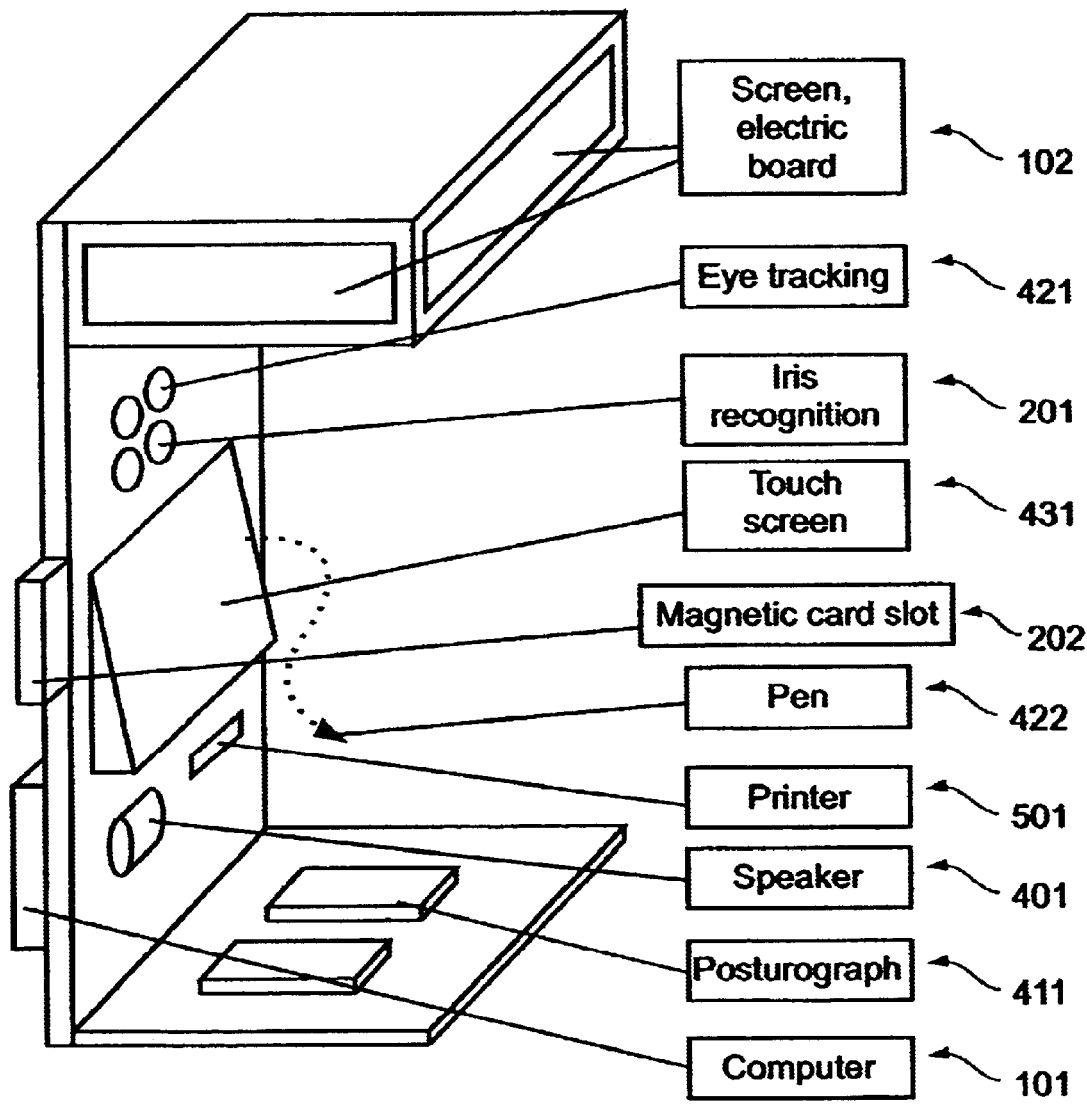
FIG. 1 is a schematic diagram illustration of the alert meter apparatus constructed and operative in accordance with a preferred embodiment of the present invention.

In accordance with a preferred embodiment of the present invention, a system for automated self-measurement of alertness, equilibrium and coordination is provided. FIG. 1 is a schematic diagram illustration of the alert meter apparatus of the present system, constructed in accordance with a preferred embodiment of the present invention. The apparatus comprises the following components: processing unit (computer) (101), testing booth, screen or electric board (102), iris recognition device (201), magnetic card reader (202) speaker (401), posturograph (411), eye movement tracking device (421), pen or light pen (422), screen, touch screen or pre-defined electric board (431) and printer (501).

These components are generally well known in the art and commercially available and thus will only be described briefly for clarification of the present invention. For example, the iris recognition device (201) may be any suitable device for identifying unique patterns in the iris of the user, such as a retinal pattern analyzer for identifying the user based on unique features in his retinal pattern.

It will also be appreciated by persons skilled in the art that the present invention is not limited by the self tester described FIG. 1, but that the self-tester may be designed and configured for any number of alternative tests.

Figure 2:
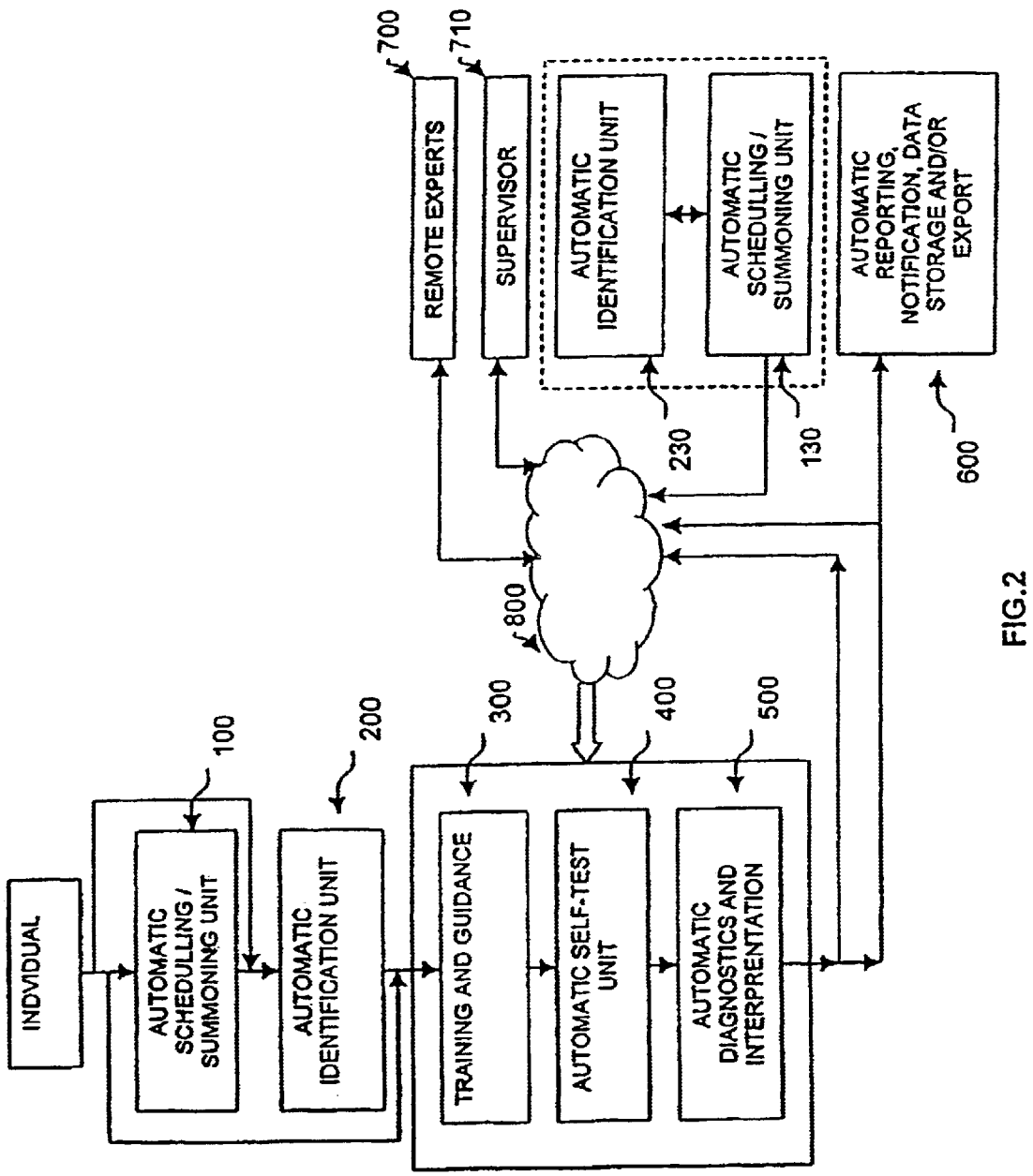
FIG. 2 is a flow chart illustration of the examination steps using the alert meter apparatus of FIG. 1.

FIG. 2 is a schematic block diagram illustration of examination steps which may be used with the self tester of FIG. 1. The examination steps are given as a non-limiting example only and include scheduling (step 100), identification (step 200), training and guidance (step 300), self-testing (step 400), interpretation (step 500), filing and notification (step 600).

Examinations can be fully automated by using all above-mentioned steps. Thus, performing the test to a pre-defined group of people automatically, such as employees at workplace, students in a school, drivers in a transportation company, and pilots in airline company. Automatic identification (230) and scheduling (130) may also be performed.

When not using the apparatus for summoning and identification, it can be used as a self-tester for checking alertness and coordination.

Vision self-testing can be performed according to the described in PCT application WO98/02083 or using any suitable display unit instead of drum or slides. For example, the display unit can be:

one or two (one for each eye) LCD screens, which can be controlled directly by micro-processor or a computer.

Apparatus which is held like glasses (such as the commonly referred to virtual reality glasses) in front of the eyes. In this case, a display unit is visible in front of each eye of the person being tested. The display units are controlled by a micro-processor or by a computer the sends and receives signals using any suitable technique known in the art, such as direct wired connection or infra-red and radio frequency wireless communication, Response of the person being tested can be either as described in PCT application WO98/02083 (by a special designed keyboard) or using other techniques (E.G. regular PC keyboard, verbal answers, which will be received and analyzed by a voice recognition unit). The special keyboard as above-mentioned can be connected by a wire to the apparatus or can send person being tested's response by various means of wireless connection.

The response of the person being tested can be either as described in PCT application WO98/02083 (for example, using a special designed keyboard) or using other suitable techniques such as regular PC keyboard, verbally (received and analyzed by a voice recognition unit). The special keyboard as above-mentioned can be directly connected to the apparatus or the response of the person being tested can be sent by wireless means or via the Internet.

As described in PCT application No. WO98/02083, the location of the self tester and the means of scheduling notification include:

1. Time clock—screen can be used to display information to summon person for testing.
2. Screen or electric board above the site of test (for example, in the entrance of the workplace or workplace's dining room)
3. Using the identification system of employees in the workplace (for example, smart card recognition, voice recognition and fingerprints)

Examples of methods of notification include:

1. Visual message—screen, electric board.
2. Audio message

Selection may be made according to any suitable criteria, such as, a fixed number or percentage of individuals to be tested—randomly, alphabetically, social security number, I.D. number or the last digits of a driving license number.

Automatic identification of the individual at the site of the alertness test before and during the test to avoid identification errors or deceits (e.g. Iris recognition, palm, fingerprint or face pattern recognition).

A description of the sequence of an exemplar sequence of tests is illustrated with reference to the flow charts of FIGS. 3 and 4.

The selection of tests can be random or pre-defined. In the example of FIGS. 3 and 4, the various steps for each of posturography (410), eye movement tracking (420) and eye-hand coordination (430) tests are illustrated. It will be appreciated that any number of different tests may be selected. In these tests, multimedia training, such as audio and visual means, and the utilization of text and pictures for demonstration purposes can be utilized.

Figure 3:
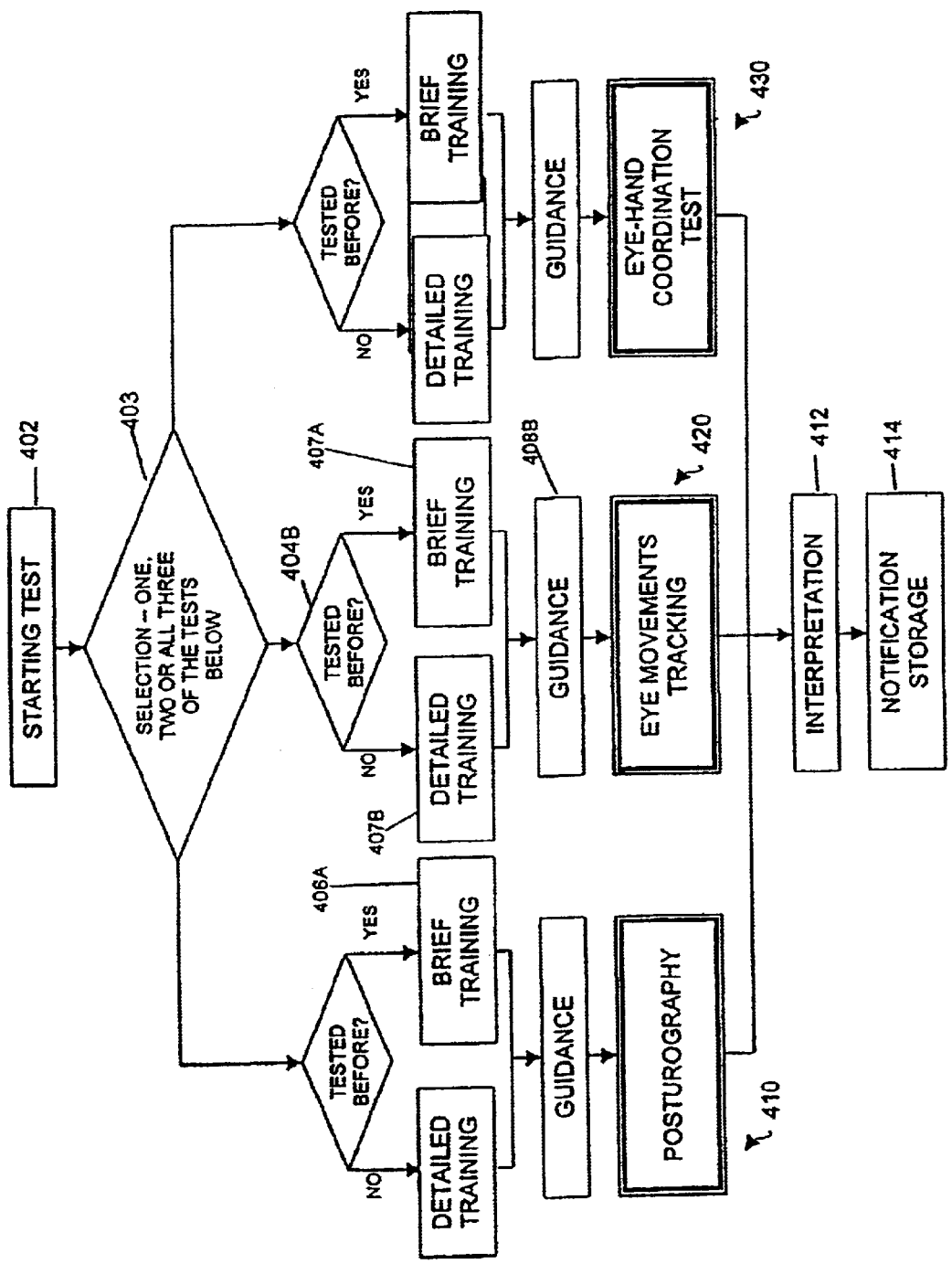
FIG. 3 is a flow chart illustration of an exemplar sequence of tests.

As shown in FIG. 3, to commence testing (step 402, the person being tested has the option of selecting in which of the tests he wishes to be examined (query box 403). For each of the tests (posturography (410), eye movement tracking (420) and eye-hand coordination (430), the person being tested is directed to either a brief (406 a/b/c) or more detailed (407 a/b/c) training, depending on whether or not (query box 404 a/b/c) he has been tested before. The suffixes a/b/c refer to either of the (posturography (410), eye movement tracking (420) and eye-hand coordination (430) tests.

Guidance and instruction (step 408 a/b/c) is displayed during the test. After the tests have been completed, the test results are interpreted (step 412) and the results stored for future retrieval (step 414).

Exemplary, instructions (in guidance step 408) are as follows:

EXAMPLE 1

Posturography

"Stand steady on foot pads, as shown on the screen.
"→"Look into the holes in front of you"
"→" "Stand steady, without moving, for XX seconds, while looking into the holes constantly."

EXAMPLE 2

For eye-hand coordination test (430), for example, multimedia training can be utilized, exemplar instructions include:

"Please find the pen hung beside the screen
→"You are supposed to draw a line in a continuous movement between the two parallel lines drawn on the screen, without touching any of them. Now you can see a short demonstration of the test.
→"Now try it yourself."

Apparatus can use various existing alertness tests, such as response speed, details perception, pulse changes according to various stimulation, questionnaires, walking foot-by-foot on a marked line, eye movement tracking, equilibrium system test (E.N.G., Posturography), eye-hand coordination.

Examples of Test Procedures

1. Posturography (410)

Examinee should stand steady on footpads for XX seconds. The posturography device is any known in the art device, such as the posturography device commercially available from Tetrax Ltd., Ramat-Gan, Israel.

2. Eye Movement Tracking (420)

Using a device that can detect the eyes position in various time frames (0.01 sec–1 sec). Devices, which are commercially available, include those manufactured by Applied Science Laboratory, of Bedford, Mass., USA and from I Scan Inc., from Barlington, Mass., USA.

Eye-hand Coordination (430)

Software that draws different drawing of two parallel lines randomly. The software checks for continuity and pauses of movement (hesitation in movement), and passing over the lines.

Figure 4:
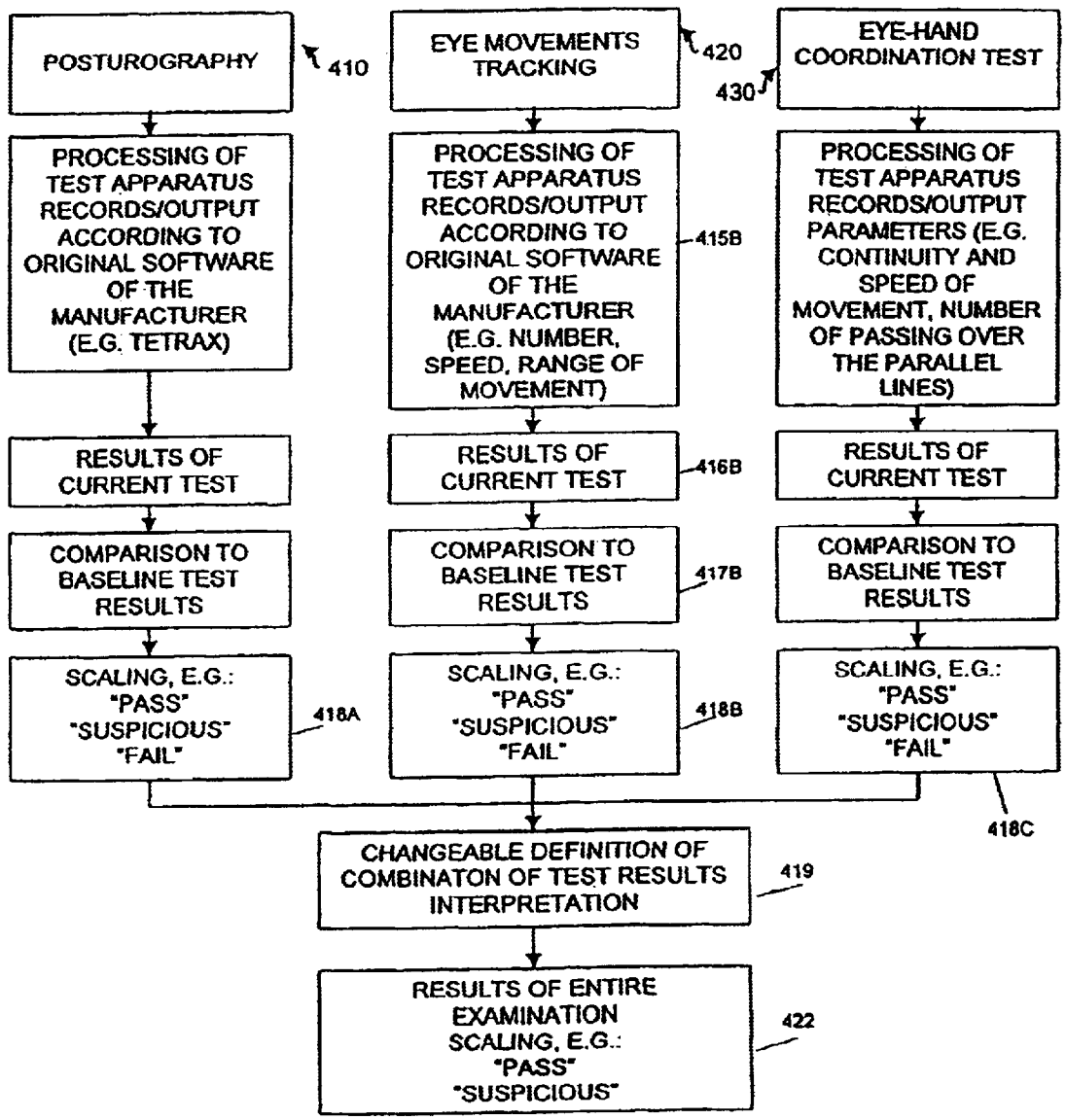
FIG. 4 is a flow chart illustration detailing the steps for the exemplar sequence of tests of FIG. 3.

As illustrated in FIG. 4, for each of the tests (posturography (410), eye movement tracking (420) and eye-hand coordination (430), the interpretation process (412 a/b/c) is similar.

The test results (step 416) are interpreted according to the Manufacturer' software and instructions (step 415). Test results are then compared to average results in population (according to sex and age), or to a baseline of the individual (step 417). The baseline is recorded when the individual is alert, with no influence of alcohol, drugs or medication.

Results are shown as "PASS" or "SUSPICIOUS" or alternatively, as a relative scale (step 418). Results can be stored and/or printed (step 414).

The combination of the various test results (418 a/b/c) are then analyzed (step 419) to produce a summary result (step 422).

Test results can be reported in various forms (i.e. direct line, telephone line, computer network, Intranet, Internet (800—FIG. 2) to various locations (i.e. clinic, experts 700, safety supervisor 710, management of the organization).

Prior to testing, the identity of the person being tested needs to be verified. In addition, it is necessary to verify that the person attending the test at a particular time is in fact the person who has been summoned for that time. This is especially important for automatic summoning and identification.

Figure 5:
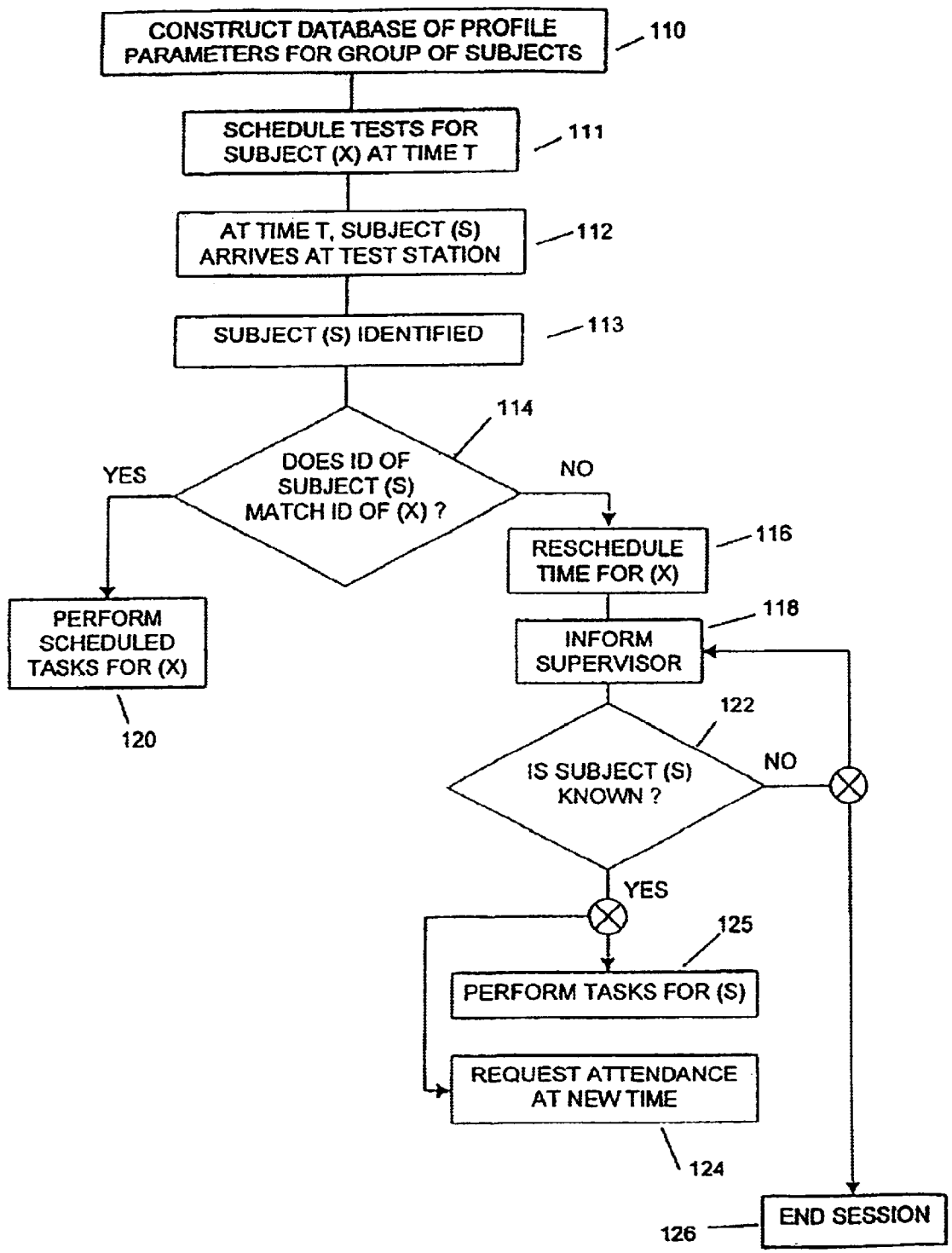
FIG. 5 is a flow chart illustration of the operation of the automatic summoning and identification of a person, constructed and operative in accordance with a preferred embodiment of the present invention.

Reference is now made to FIG. 5, which is a flow chart illustration of the operation of the automatic summoning (100) and identification (200) of a person to be tested or to perform certain tasks or procedures.

A database of profile parameters including the physical characteristics of persons as well as their personal details needed for automatically summoning them is initially constructed (step 110), as described in PCT application WO98/02083.

A schedule is prepared automatically summoning persons to attend at scheduled times (step 111), to take part in tests or carry out a series of tasks, for example. At a scheduled time T, a subject (X) (say) has been summoned to attend the test/task station.

At the scheduled time T, a subject (referenced S) arrives and presents himself (step 112). The subject (S) presenting himself is identified (step 113) by any of the methods, described hereinabove, such as voice recognition, iris recognition and fingerprinting.

The results of the identification (or profile) of subject (S) are then checked against the ID details in the database of profile parameters (query box 114)

If there is a positive identification, that is if the profile of the attending subject (S) is found to match the profile of the summoned subject (X), the scheduled tests (for example, a series of tests for alertness) for which (X) was summoned are carried out (step 120). An example of the examination steps is described hereinabove with respect to FIG. 2 and include training and guidance (step 300), self-testing (step 400) and interpretation (step 500), If the identification results are negative, the supervisor is informed (step 118) and a new time for summoning X is scheduled (step 116).

Furthermore, if the profile of the attending subject (S) is found not to match the profile of the summoned subject (X), (that is after step 114), but matches one of the profile stored in the database, several alternative steps may be performed. The subject may be allowed to perform the set of tasks scheduled for subject (S) or subject (S) can be requested to attend at another scheduled time (step 124).

If the profile of the attending subject (S) does not match any of the known profiles stored in the database, the supervisor is informed (step 118) and/or the session is terminated (step 126).

The identity of a known person, who has previously been tested, can be checked, for example by requesting the person to respond to various random questions. The answers can then be compared with the data stored from previous test results.

To prevent a person from memorizing the order of questions and answers, in a series of tests, visual test images can be used. For example, the optical testing unit presents at least one eye of the user with visual test images including a single test pattern and a multiple-choice answer pattern, receives answers selected by the user and analyzes the answers to determine the test result. The visual test images may be randomly or pseudo-randomly selected from a predetermined group of images for preventing the user from predicting the answers.

It is a feature of the present invention that the system can continuously verify the identity of the person being tested or performing a set of tasks and thus prevent abuse of the tests by, for example, another person standing in for the person being tested once the person has been identified. Any of the previously mentioned systems for identifying a person may be used, such as voice recognition, iris recognition and fingerprinting. Alternatively, the person being tested can be presented with a random or pseudo-random selection of different questions specifically to verify that the person answering these questions is the same person who 'logged' on and was initially identified.

Figure 6:
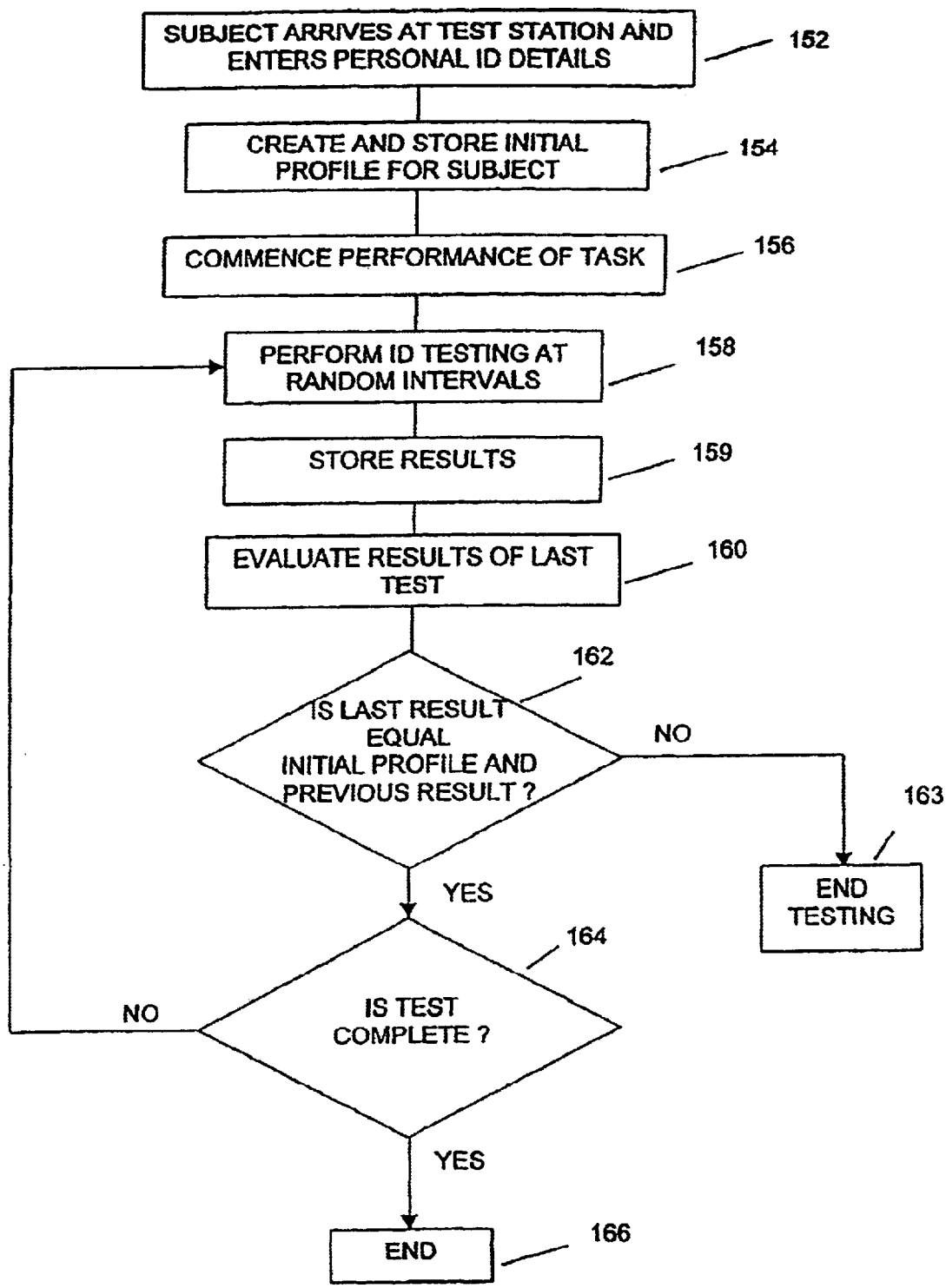
FIG. 6 is a flow chart illustration of an exemplar method of the operation of continuously verifying the identity of a person performing tasks or attending a test station, constructed and operative in accordance with a preferred embodiment of the present invention.

Reference is now made to also made to FIG. 6, which a flow chart illustration of an exemplar method of the operation of continuously verifying the identity of a person performing tasks or attending a test station.

The subject on arriving at the test/task station to carry out scheduled tests (step 112), or perform a series of designated tasks (or tests), for example, enters his personal ID details (step 152).

An initial profile of the subject is created (step 154) and stored, the profile including personal characteristic parameters (hereinafter referred to as ID tests), such as voice recognition, iris recognition, fingerprinting and photographic images.

The subject commences the set tasks (step 156). At various random intervals during the performance of these tasks, the subject is again identified (step 158) and the results stored (step 159). Each of these random ID tests are evaluated (step 160). Only if the there is a match (query box 162) do the tests or tasks continue, until the task have been completed (loop 158–164). Otherwise, the continuous loop ends (step 163).

Figure 7:
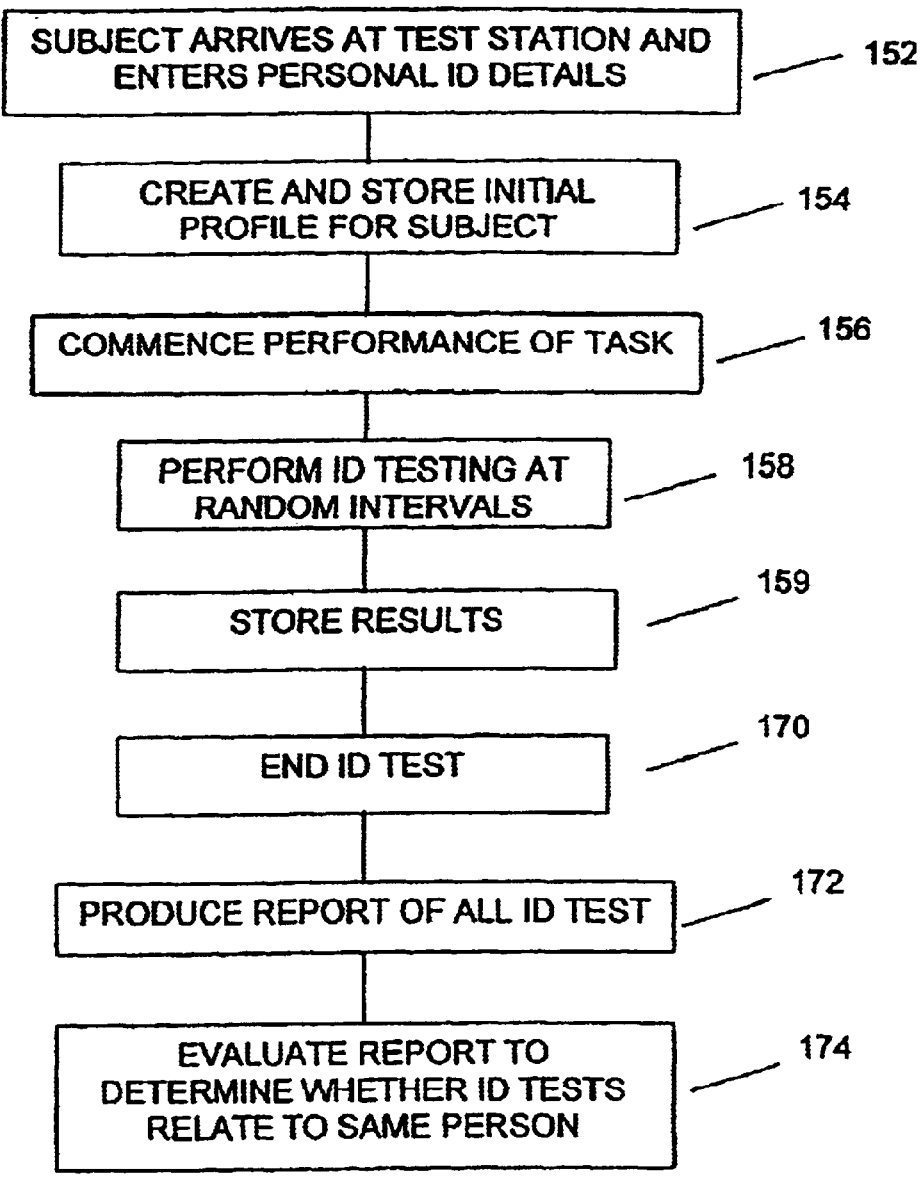
FIG. 7 is a flow chart illustration of an exemplar method of the operation of continuously verifying the identity of a person performing tasks or attending a test station, constructed and operative in accordance with a further preferred embodiment of the present invention.

An alternative embodiment method, of the operation of continuously verifying the identity of a person performing tasks or attending a test station, is illustrated in the flow chart of FIG. 7.

This alternative method is particularly useful for verifying the identity of a person by photographs or video, for example, and which do not have to rely on an automatic verification process.

The method is similar to the method described with reference to FIG. 6 and similar reference numerals (for similar steps) have been used where applicable.

The subject on arriving at the test/task station enters his personal ID details (step 152). An initial profile of the subject, using photographs or video frames, for example, is created (step 154) and the results stored.

The subject commences the set tasks (step 156). At various random intervals during the performance of these tasks, the subject is again identified (step 158) and the results stored (step 159).

At the end of the ID test (170), a report of the tasks (or tests) can be produced together with a series of identifying images, such as photographs or video frames, taken during the carrying out of the various tasks/tests. A supervisor or examiner can then manually check the identifying images (step 172).

In a further embodiment of the present invention, the testing procedure system may be used to verify that: the subject has understood the limitations of the test he is undertaking and the contents of a document containing disclaimers which he is asked to sign. For instance, prior to taking a test, the subject can be requested to read a document having certain disclaimers. In order to check whether he understands the document and the limitations detailed therein, he can be randomly asked questions from a group of questions. By analyzing the answers, a person's comprehension can be easily verified. This type of verification system is useful in many applications, such as commercial transactions and medical tests carried out by the use without direct medical supervision. A particular use is in e-commerce, that is transactions carried out over the Internet. At present, a purchaser of goods via the Internet only needs to click his acceptance of the deal. The store or seller, however, does not know whether the purchaser has read the terms and conditions and whether he understands them. By the addition of active verification, whereby the purchaser has to answer random questions to ascertain his understanding, a further level of the 'meeting of minds' in commercial transactions is added. This can prevent misunderstandings between the parties concerned and consequent expense and lawsuits, for example.

For example, a patient using the ECG testing equipment, described in U.S. patent application Ser. No. 09/428,430, can be asked a random set of questions prior to the use of the equipment to check that he understands the limitations of the home test. In order to verify that the patient has read the disclaimer, for example advising him to seek medical advice in the event of not feeling well and not to rely on a negative ECG test as an indication of "everything being OK", part of the testing procedure could require him to answer random questions, such as multiple choice questions, related to the form he is to sign and the contents therein.

It will also be appreciated by persons skilled in the art that the present invention is not limited by what has been particularly shown and described herein above. Rather the scope of the present invention is defined only by the claims which follow.

What is claimed is:

1. A system for continuously verifying the identity of a person being tested, comprising:

an identity testing unit for carrying out an initial identification test to identify a person and subsequent identification tests at random intervals over a testing duration, therefrom to build an identification profile covering said duration;

at least one physiological testing unit for performing at least one physiological test on said person being identified over said duration of said identification tests, said physiological test being selected randomly from a group of physiological tests;

an interpretation unit for evaluating the results of said identification test to obtain an identification profile of the person being tested over said duration and for evaluating the results of said at least one physiological test performed over said duration;

a storage unit for storing said identification profile and said at least one physiological test result; and a comparison unit for comparing identification data of said initial and subsequent identification tests of said identification profile.

2. A system according to claim 1, wherein said at least one physiological test comprises one of a group of tests including a person's alertness, steadiness, co-ordination and response time.

3. A system according to claim 1, wherein said interpretation unit is further operable to evaluate said at least one physiological test to determine therefrom whether a person is under the influence of external substances or stimulants.

4. A system according to claim 1, wherein said physiological testing unit is configured to select a plurality of physiological tests from said group of physiological tests and said interpretation unit is correspondingly configured to evaluate the results of the plurality of physiological tests individually and/or in any combination thereof.

5. A method for continuously verifying the identity of a person performing a task randomly selected from a group of tasks, the method comprising the steps of:

creating and storing an initial profile of personal characteristics associated with the person, prior to performing the randomly selected task;

continuously performing at least one identification test at random intervals while the person performs said randomly selected task;

storing the results of each of said randomly performed at least one identification test;

comparing the results of each of said randomly performed at least one identification test with the initial profile and with previous randomly performed identification tests after each randomly performed at least one identification test; and evaluating a result of said randomly selected task.

6. A method according to claim 5 wherein said comparing of results is automatic and the method further comprises the step of:

if the results of said automatic comparison match the at least one identification test with the initial profile, allow the person to perform said randomly selected task.

7. A method according to claim 5 and further comprising the step of:

comparing the initial profile of personal characteristics with a database of personal characteristics of a group of persons to ascertain the identity of the person.

8. A method according to claim 5 wherein said profile comprises at least one of a group comprising voice recognition patterns, iris patterns and photographic images.

9. A method according to claim 5 wherein said step of determining an initial identification profile comprises:

identifying the person to be tested;

performing at least one identification test;

evaluating the results of said at least one identification test to obtain the initial identification profile; and storing said results for later retrieval.

10. A method according to claim 5 wherein said randomly selected task comprises one of a group of tasks for testing a person's alertness, steadiness, co-ordination and response time.

11. A method according to claim 9 wherein said at least one randomly selected task comprises one of a group of tasks for testing a person's alertness, steadiness, co-ordination and response time.

12. A method according to claim 9 and further comprising the step of evaluating said tasks in relation to said stored results.

13. A method according to claim 5 wherein said step of evaluating is operable in real time or off-line.

14. A method according to claim 5 wherein said step of evaluating comprises the step of determining whether a person is under the influence of external substances or stimulants.

15. A method according to claim 5 wherein said step of evaluating comprises the step of evaluating the results of the randomly selected tasks individually and/or in any combination of tasks.

16. A method according to claim 5 wherein said at least one identification test comprises at least one of a group of tests including photographing the attending person at random intervals, requesting the person to respond to various random questions, iris recognition, palm, fingerprint or face pattern recognition.

17. A method for continuously verifying the identity of a person performing a selected task, the method comprising the steps of:

selecting a task from a group of tasks;

creating and storing an initial profile of personal characteristics associated with the person prior to performing the task;

performing at least one identification test at random intervals while the person performs said task;

storing the results of each of said randomly performed said at least one identification test;

evaluating results of said task; and comparing the results of each of said randomly performed at least one identification test with the initial profile at the completion of said task.

18. A method according to claim 17 wherein said profile comprises at least one of a set of parameters including voice recognition patterns, iris patterns and photographic images.

* * * * *